(12) United States Patent
Rigaux

(10) Patent No.: US 9,987,486 B2
(45) Date of Patent: Jun. 5, 2018

(54) METHOD FOR THE TREATMENT OF CONSCIOUSNESS DISORDERS

(71) Applicant: Cefaly Technology Sprl, Seraing (BE)

(72) Inventor: Pierre Rigaux, Liège (BE)

(73) Assignee: CEFALY TECHNOLOGY SPRL, Seraing (BE)

( * ) Notice: Subject to any disclaimer, the term of this patent is extended or adjusted under 35 U.S.C. 154(b) by 24 days.

(21) Appl. No.: 15/250,431

(22) Filed: Aug. 29, 2016

(65) Prior Publication Data
US 2018/0056059 A1 Mar. 1, 2018

(51) Int. Cl.
| A61N 1/00 | (2006.01) |
| A61N 1/20 | (2006.01) |
| A61N 1/04 | (2006.01) |
| A61N 1/22 | (2006.01) |
| A61N 1/36 | (2006.01) |
| A61N 1/24 | (2006.01) |

(52) U.S. Cl.
CPC .......... *A61N 1/205* (2013.01); *A61N 1/0456* (2013.01); *A61N 1/0476* (2013.01); *A61N 1/0484* (2013.01); *A61N 1/22* (2013.01); *A61N 1/36025* (2013.01); *A61N 1/24* (2013.01); *A61N 1/36034* (2017.08)

(58) Field of Classification Search
CPC .. A61N 1/0526; A61N 1/0529; A61N 1/0531; A61N 1/36025; A61N 1/36082; A61N 1/20; A61N 1/205; A61N 1/18; A61N 1/0456
See application file for complete search history.

(56) References Cited

U.S. PATENT DOCUMENTS

| 8,583,238 B1 | 11/2013 | Heldman et al. |
| 2010/0113959 A1* | 5/2010 | Pascual-Leone ...... A61N 2/006 600/544 |
| 2015/0066104 A1* | 3/2015 | Wingeier ............. A61B 5/4064 607/45 |

FOREIGN PATENT DOCUMENTS

| CN | 102698360 A | 10/2012 |
| WO | WO 2008/005478 A2 | 1/2008 |
| WO | WO 2009/137683 A2 | 11/2009 |
| WO | WO 2013/022840 A1 | 2/2013 |

OTHER PUBLICATIONS

Angelakis et al., "Transcranial Direct Current Stimulation Effects in Disorders of Consciousness", Archives of Physical Medicine and Rehabilitation, 95:283-289, 2014.
Notification of Transmittal of the International Search Report & the Written Opinion in International Patent Application No. PCT/IB2017/054905, dated Nov. 7, 2017.

* cited by examiner

Primary Examiner — Scott Getzow
(74) Attorney, Agent, or Firm — Knobbe Martens Olson & Bear LLP

(57) ABSTRACT

The present invention provides a method for the treatment of consciousness disorder comprising the steps of positioning at least two electrodes on a patient's head such that the first electrode is positioned on the right supraorbicular cortex and the second electrode is positioned on the left dorso-lateral prefrontal cortex; connecting said electrodes to at least one source of electrical current; delivering direct current to the electrodes, and removing the electrodes from the patient's head after a time T; wherein steps a) to d) represent a treatment session and wherein at least one treatment session is is applied on the patient's head at least 2 days per week.

11 Claims, 2 Drawing Sheets

METHOD FOR THE TREATMENT OF CONSCIOUSNESS DISORDERS

FIELD OF THE INVENTION

The present invention pertains to a non-invasive method for the treatment of consciousness disorders. The method uses transcranial direct current stimulation (tDCS).

BACKGROUND

In recent years, resuscitation techniques have led to a considerable increase in the number of patients who survive severe brain injuries. Some patients recover in the first days after the injury others die quickly. Others, however, recover more slowly through different stages before fully or partially recovering consciousness. Patients having consciousness disorders present major challenges concerning the diagnosis, prognosis, daily care and treatment.

Disorders of consciousness include coma and the vegetative state (VS). Patients in coma have complete failure of the arousal system with no spontaneous eye opening and are unable to be awakened by application of vigorous sensory stimulation. VS is characterized by the complete absence of behavioral evidence for self or environmental awareness. There is preserved capacity for spontaneous or stimulus-induced arousal, evidenced by sleep-wake cycles.

Some patients with severe alteration in consciousness have neurologic findings that do not meet criteria for VS. These patients demonstrate discernible behavioral evidence of consciousness but remain unable to reproduce this behavior consistently. This condition is referred to here as the minimally conscious state (MCS). MCS is distinguished from VS by the partial preservation of conscious awareness.

Non-invasive interventions have been used to improve the functional level MSC patients. Said interventions are based on neuromodulation which includes the broad category of "transdermal electrical stimulation," referring to the electrical stimulation of the nervous system (brain, cranial nerves, peripheral nerves, etc.) through a subject's skin. Specific examples of transdermal electric stimulation (hereinafter "TES") may include transcranial stimulation, for example, through scalp electrodes and have been used to affect brain function in humans in the form of transcranial alternating current stimulation, transcranial direct current stimulation (hereinafter "tDCS"), cranial electrotherapy stimulation, and transcranial random noise stimulation.

Despite several research and clinical trial on non-pharmacological treatments, there is currently no effective standardized treatment and no evidence-based treatment for patients suffering from consciousness disorder, in particular minimal consciousness state (MCS).

The aim of the present invention is to provide a solution to overcome at least part of the above mentioned disadvantages. The invention thereto provides a treatment method as described below and as defined by the appended claims.

SUMMARY

The invention provides a method for the treatment of consciousness disorder comprising the steps of:
a) positioning at least two electrodes on a patient's head such that the first electrode is positioned on the right supraorbicular cortex and the second electrode is positioned on the left dorso-lateral prefrontal cortex;
b) connecting said electrodes to at least one source of electrical current;
c) delivering direct current to the electrodes, and
d) removing the electrodes from the patient's head after a time T;
wherein steps a) to d) represent a treatment session and wherein at least one treatment session is applied on the patient's head at least 2 days per week.

The invention provides several advantages compared to the methods of the prior art. The method of the invention is safe, non-invasive and drug free. The method is highly efficient as the consciousness level of treated patients has been considerably improved which leads to a better life quality thanks to the possible communication with family members for instance.

DETAILED DESCRIPTION OF THE INVENTION

Figure 1:
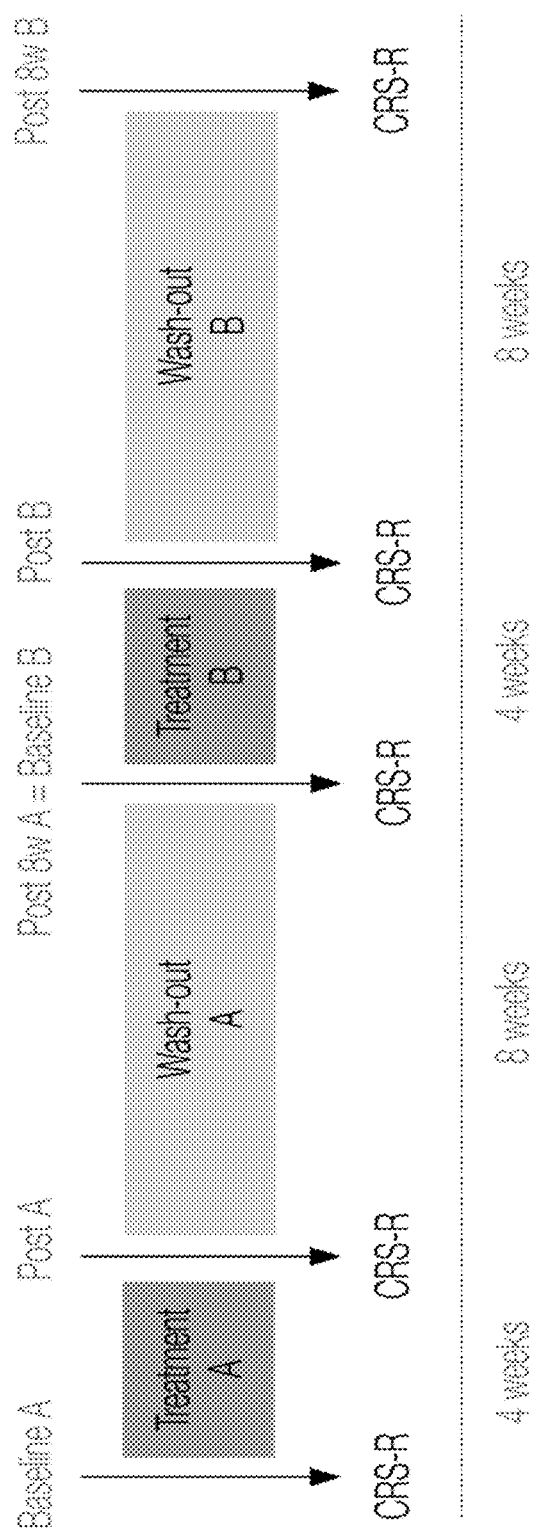
FIG. 1 shows time scale of the applied treatment and the CRS-R measurements.
Figure 2:
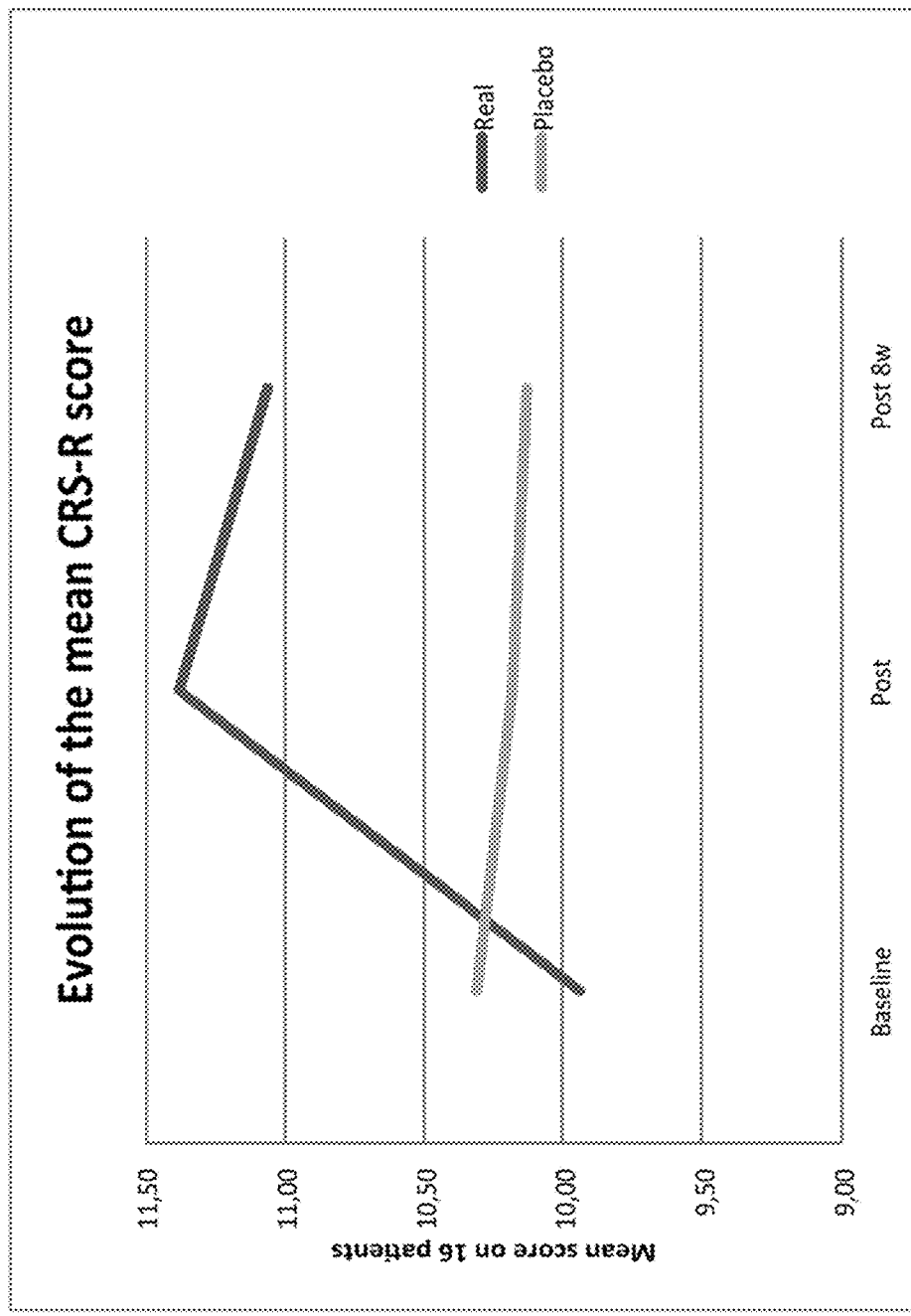
FIG. 2 shows the effect of the method of the invention on patient having MCS (i.e., the evolution of the CRS-R measurements for both type of treatment).

The present invention relates to a non-invasive method for the treatment of consciousness disorder. The method uses transcranial current stimulation for said treatment.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

In a first aspect, the present invention provides a method for the treatment of consciousness disorder comprising the steps of:
a) positioning at least two electrodes on a patient's head such that the first electrode is positioned on the right supraorbicular cortex and the second electrode is positioned on the left dorso-lateral prefrontal cortex;
b) connecting said electrodes to at least one source of electrical current;
c) delivering direct current to the electrodes, and
d) removing the electrodes from the patient's head after a time T;

wherein steps a) to d) represent a treatment session and wherein at least one treatment session is is applied on the patient's head at least 2 days per week.

In a preferred embodiment, one treatment session is applied at least one time every 24 hours 7 days per week, preferably for maximum 6 days per week, more preferably for maximum 5 days per week. The treatment sessions can be applied at any time of the day and are preferably applied in the morning so between 6 am and 12 am. In a preferred embodiment, the repetitive treatment sessions are applied to the patient at the same time. For instance, if the first session has been applied on Monday at 10 am, the next session is to be applied on Tuesday at 10 am.

Preferably, the time T in step d) is at least 5 minutes and at most 30 minutes, preferably at least 10 min and at most 20 min.

The intensity of the direct current is of from 0.5 to 3 mA, preferably of from 1 to 2.5 mA, more preferably about 2 mA.

Preferably, the intensity of the direct current increases progressively following a slope of from 0.06 mA/sec to 0.6 mA/sec, more preferably about 0.4 mA/sec. The intensity of the direct current increases progressively during a period of time T' wherein T' is at least 1 second and at most 5 minutes, preferably T' is about 5 seconds.

Preferably the density of the direct current is of from 0 to 100 $\mu A/cm^2$, preferably of from 50 to 60 $\mu A/cm^2$.

The treatment is applied during at least one week and at most 10 weeks, preferably at least at least 2 weeks and at most 9 weeks, more preferably at least 3 weeks and at most 8 weeks, even more preferably at least 4 weeks and at most 7 weeks, most preferably at least 5 weeks and at most 6 weeks. The treatment can also be applied for several months or several years.

EXAMPLES

Patients

A group of traumatic and non-traumatic patients in a sub-acute and chronic MSC for at least 3 months has been selected for the treatment. The group consisted of 16 patients and comprised a mix of male and female patients of different age but of at least 18 years old. Patients with a metallic cerebral implant or a pacemaker were excluded from the group. Also patients who received a drug treatment and/or suffering from other disorders, such as epilepsy, were excluded from the group.

Treatment

One treatment session consisted of positioning two electrodes on the skull of the patient. The cathode was positioned above the right eyebrows and more exactly on the right supraorbicular cortex (FP2). The anode was positioned on the left dorso-lateral prefrontal cortex (F3). The electrodes were connected to an electric current generator. Direct current having an intensity of 2 mA and a density of from 50 to 60 $\mu A/cm^2$ was delivered to the patients for 20 min. The increase in current intensity was gradual following a slope of 0.4 mA/s.

The above described treatment session has been repeated every day at the same time for 5 days per week.

Each patient received, in a random order, the above treatment for 4 weeks and a placebo treatment for 4 weeks. The placebo treatment was made of a similar setup as the real treatment, but the stimulation was only active for 5 seconds. For the rest of the 20 minutes, no direct current was delivered by the placebo treatment. The two 4-week treatments were separated by a 8-week period without treatment. The treatment was applied either by the family at home, or by a nurse in a rehab center. The caregiver was blinded on the treatment.

Results Measurement and Analysis

Treatment result was assessed based on Coma Recovery Scale Revised (CRS-R) as described in Giacino et al., 2004, *Arch Phys Med Rehabil*. The measurements were performed on each patient before the treatment (Baseline A, FIG. 1), immediately after the treatment A (Post A, FIG. 1), 8 weeks after the end of the treatment A, which corresponds to the beginning of treatment B (Post 8w A=Baseline B, FIG. 1), immediately after the treatment B (Post B, FIG. 1) and 8 weeks after the end of treatment B (Post 8w B, FIG. 1). As mentioned earlier, patients were randomly assigned either real treatment or placebo treatment as treatment A, and the other as treatment B.

The mean delta between Baseline and Post CRS-R score is $+1.44\pm2.19$ (statistically significant, $p<0.05$) for the real treatment and $-0.13\pm2.25$ ($p>0.80$) for the placebo treatment. The difference of this delta between the real treatment and the placebo treatment is also statistically significant ($p<0.05$).

At the individual level, 10 out of 16 patients, i.e. 62.5% of the patients, showed a tDCS-related improvement. This is better than with a single session where the improvement observed in only 43% of the patient (reported in Thibaut et al. 2014). Repeating the stimulation increases patient's reactivity to the treatment.

Although the present invention has been described with reference to preferred embodiments thereof, many modifications and alternations may be made by a person having ordinary skill in the art without departing from the scope of this invention which is defined by the appended claims.

What is claimed is:

1. A method for the treatment of a consciousness disorder comprising:
    a) positioning at least two electrodes on a patient's head such that the first electrode is positioned over the right supraorbicular cortex and the second electrode is positioned over the left dorso-lateral prefrontal cortex;
    b) connecting said electrodes to at least one source of electrical current;
    c) delivering direct current to the electrode, wherein an intensity of the direct current increases progressively during a period of time T', wherein T' is at least 1 second and at most 5 minutes, and
    d) removing the electrodes from the patient's head after a time T;
    wherein a) to d) represent a treatment session and wherein at least one treatment session is applied on the patient's head at least 2 days per week.

2. The method according to claim 1 wherein one treatment session is applied at least one time every 24 hours.

3. The method according to claim 1, wherein the time T in step d) is at least 5 minutes.

4. The method according to claim 1, wherein the time T in step d) is at most 30 minutes.

5. The method according to claim 1, wherein an intensity of the direct current is from 0.5 to 3 mA.

6. The method according to claim 1, wherein an intensity of the direct current is about 2 mA.

7. The method according to claim 1, wherein the progressive increase of the direct current follows a slope of from 0.06 mA/sec to 0.6 mA/sec.

8. The method according to claim 1, wherein T' is 5 seconds.

9. The method according to claim 1, wherein a density of the direct current is from 0 to 100 µA/cm².

10. The method according to claim 9, wherein the density of the direct current is from 50 to 60 µA/cm².

11. The method according to claim 1, wherein the treatment is applied during at least one week.

\* \* \* \* \*